United States Patent [19]

Blackburn

[11] 4,438,144
[45] Mar. 20, 1984

[54] AMINO ACID PREPARATION AND THERAPY FOR TREATMENT OF STRESS AND INJURY

[76] Inventor: George L. Blackburn, 100 Memorial Dr., Cambridge, Mass. 02142

[21] Appl. No.: 373,125

[22] Filed: Apr. 29, 1982

Related U.S. Application Data

[63] Continuation of Ser. No. 174,189, Jul. 31, 1980, abandoned.

[51] Int. Cl.$^3$ .......................................... A61K 31/195
[52] U.S. Cl. ..................................................... 424/319
[58] Field of Search ........................................ 424/319

[56] References Cited

U.S. PATENT DOCUMENTS

| | | | |
|---|---|---|---|
| 3,832,465 | 8/1974 | Ghadini | 424/319 |
| 3,920,838 | 11/1975 | Flott et al. | 424/319 |
| 3,950,529 | 4/1976 | Fisher et al. | 424/319 |
| 4,209,531 | 6/1980 | Berry | 424/319 |
| 4,252,822 | 2/1981 | Berry | 424/319 |

FOREIGN PATENT DOCUMENTS 2440194 10/1979 France .

OTHER PUBLICATIONS

Surgery, Aug. 1976, vol. 80, No. 2, pp. 192–200.
Surgery, Aug. 1979, vol. 86, No. 2, pp. 307–315.
Chang et al., The Journal of Biol. Chem. 253010, 3696–3701, ( 5–78).
Hedden et al., Soc. for Exp. Biology & Medicine 410–415, (1979).
Berrotti et al., Surgical Forum, 27, 7–10, (1976).
Sakamoto et al., Surgical Forum, 30, 67–69, (1979).
Yoshimura et al., The Journ., of Parenteral & Ent. Nutrition, pp. 525–531.
The Health Quarterly (1979), p. 54.

*Primary Examiner*—Stanley J. Friedman
*Attorney, Agent, or Firm*—Donald Brown; Robert Goldberg

[57] ABSTRACT

Disclosed is a novel nutritional branched chain amino acid composition and its use for treatment of a patients suffering stress or injury, especially useful for parenteral or enteral alimentation of a patient suffering total or partial dysfunction or disuse of the gastrointestinal tract. The novel composition promotes and even optimizes patient wound healing, immune competence, host defense, and/or survival. The amino acids comprise from about 70 to 100% valine, isoleucine, and leucine, collectively, in a ratio of A:B:C, respectively, where A, B and C each independently has value from about 1 to 2. The novel composition is preferably used in the form of a parenteral infusion solution of from about 2 to 6%, most preferably 4% concentration.

5 Claims, 13 Drawing Figures

PROTEIN SYNTHESIS RATES IN PANCREATITIS RATS

FIG. 9 — UPPER SMALL INTESTINE

FIG. 10 — PANCREAS

AMINO ACID PREPARATION AND THERAPY FOR TREATMENT OF STRESS AND INJURY

This is a continuation, of application Ser. No. 174,189 filed July 31, 1980, now abandoned.

BACKGROUND OF THE INVENTION

Introduction

This invention relates to a novel amino acid composition and its use in a method of treating a patient for stress or injury. More specifically, it relates to a branched chain amino acid composition having a pharmacological effect for treatment of patients suffering illness, sepsis, trauma or other injury.

Description of the Prior Art

The metabolic response to injury consists of many processes which have evolved over millions of years. The metabolic changes are best understood as a redistribution of nutrients from labile reserves to more active tissues for host defense and recovery. Other metabolic responses to injury include hyperglycemia, increased rates of lipolysis, gluconeogenesis, and glycogenolysis (Blackburn, G. L., Phinney, S. D., *Surgical Physiology*, Edited by Burke J. F., Philadelphia, C. V. Mosby and Co., 1980; Wilmore, D. W. *Surg. Clin. North Am.* 56, 999, (1976). In addition to increased amino acid catabolish, there is significant mobilization and redistribution of body protein. Micronutrients such as zinc are also redistributed and increased uptake by the liver is important in potentiating enzymatic functions required during injury (Pekarek, R.S., Wannemacher, R. W., Jr., Beisol, W. R. *Proc. Soc. Exp. Biol. Med.*, 140, 685, 1965). Increased hepatic synthesis of iron-binding proteins aids lymphocyte function as well as reducing the quantity of free iron available in pathogenic micro-organisms. Increases in plasma copper concentration in the form of ceruloplasmin may be involved in the regulation of catecholamines, prostaglandins, and serotonin (Powanda, M. C., Kenyon, R. H., Moe, J. B. *Proc. Soc. Exp. Biol. Med.* 151, 804, 1976).

Stress of injury such as trauma or sepsis often is accompanied by partial or complete dysfunction of the gastro-intestinal tract. Patients suffering such dysfunction or who are subject to disuse of the gastro-intestinal tract because of physician's prescription are obliged to receive most or all of their daily nutritional requirements parenterally and/or enterally. The object is to provide the patient with as much of the normal daily nutritional requirements as possible to sustain protein synthesis and avoid malnutrition. At the same time, energy expenditure and protein turnover are often increased. Thus, the body is often required to draw upon its own resources to meet its metabolic needs. In uninjured man, mobilization of fat reserves occurs within a few days of calorie restriction and is effective in minimizing protein losses. However, the adaptive procedure is much less efficient in severe stress or injury, such as infections, thermal injury, and sepsis, where net loss of lean body mass may exceed 500 g/day (15–20 g urinary nitrogen excretion/day). This decreased ability of injured or infected organisms to utilize amino acids for protein synthesis is a contributing factor in increase morbidity and mortality of serious ill patients.

In the past, infusion solutions used for intravenous feeding having conventionally comprised an aqueous solution of a carbohydrate of high caloric content such as sucrose, glucose or the like. Such methods of treatment are shown by Dudrick et al, "Total Intravenous Feeding", *Scientific American* 73 (May, 1972), which suggests the infusion of 1000 calories (glucose) per liter of nutrient solution, and Shils, "Guidelines for Total Parenteral Nutrition", *J. American Med. Assoc.* 220 (B) (1972).

It is known in the art, however, that during prolonged periods of illness, and notwithstanding conventional intravenous feeding, there can be a significant loss of body weight. A portion of this loss can be attributed to the mobilization of stored fat, which is not a serious health problem. Another portion of the loss in body weight, however, is attributable to a loss in the lean body mass, i.e., muscle, organs, etc. This loss correlates to a loss of body nitrogen. More specifically, during a period of negative caloric balance, the lean body mass breaks down releasing amino acids which are converted by the liver into glucose and urea, the urea being excreted in urine. By determining the nitrogen content in urine, the decrease in lean body mass can be determined. By this method, a nitrogen balance can be made. A negative nitrogen balance means a loss in lean body mass—i.e., the body is losing more nitrogen that it is taking in. This is a very serious problem as a sustained loss in lean body mass can result in morbidity, even mortality. Protein depletion, particularly of visceral organs, represents the single most important aspect of trauma today. Thus, if a seriously ill patient, fed intravenously, loses about 30% of his original body weight, death is likely. (Studley, H. D., "Percent of Weight Loss: A Basic Indicator of Surgical Risk, "*Journal American Medical Assoc.* 106: 458, and Taylor and Keyes, "Criteria of Physical Fitness in Negative Nitrogen Balance, " *Ann. N. Y. Ac'D Sci.* 73:465, (1958).

To avoid losses in lean body mass, it is the practice to supplement the compositions used for parenteral feeding (the infusion solutions) with amino acids to replace the amino acids secreted by the lean body mass. A typical nutritional infusion solution comprises an aqueous solution of carbohydrates, fats and amino acids. However, even when amino acids are parenterally administered with the infusion solution, as aforesaid, a negative nitrogen balance often is still encountered over a sustained period of time, with a concomitant reduction in lead body mass, though the negative nitrogen balance might not be as severe as it would be in the absence of the infused amino acids. Thus, the period of time that parenteral feeding can be utilized as a sole means of nutrition is extended by the use of amino acids, but for many illnesses, the period of time is not extended sufficiently to avoid the serious effect of a prolonged net negative nitrogen balance.

In U.S. Pat. No. 3,920,838, the disclosure and teaching of which, in its entirety, is incorporated herein by reference, an amino acid therapy was disclosed for patients during periods of severe negative caloric intake due to dysfunction or disuse of the gastro-intestinal tract, which method is a radical departure from prior methods. That method comprises parenteral feeding of amino acids to the patient while substantially elminating other sources of high caloric nutrition (such as glucose) during the period in which the patient is parenterally fed, thereby intentionally creating a condition simulating starvation ketosis. Thus, the method has for an object during a condition simulating starvation ketosis, whereas the prior methods have for an object avoidance of starvation (Dudrick et al and Shils, supra). That novel hypocaloric method of treatment is based in part on the recognition that starvation ketosis occurring during severe negative caloric balance allows more adequate fat mobilization, whereby endogenous fat stores meet almost all the patient's energy requirements with little or no catabolism of lean body mass protein. Parenteral administration of carbohydrate, on the other hand, often is not possible in sufficient amount to meet energy requirements, and yet acts to impede fat mobilization. Consequently, such parenteral administration of carbohydrate has the counter-productive effect of causing protein catabolism and net nitrogen loss.

Thus, in accordance with that novel hypocaloric method of treatment, a patient can survive longer during periods of disuse of the gastro-intestinal tract, even though suffering starvation ketosis, then with conventional methods, because the method avoids losses in the lean body mass. The explanation is a substantial oversimplification of the body chemistry involved during starvation ketosis. A more complete and accurate description is set forth in the specification of U.S. Pat. No. 3,920,838.

Beyond the advance disclosed in U.S. Pat. No. 3,920,838, there remains considerable uncertainty as to the optimal nutritional regimen for parenteral administration to a patient. For lack of a more sound basis, amino acid solutions for intravenous alimintation in the past have been based on an analogy with experimentally derived oral requirement or with the amino acid content of normal body fluid. These known solutions are formulated, however, for use in conjunction with other sources of nutrition, including typically a carbohydrate of high caloric content, such as glucose. In U.S. Pat. No. 3,832,465, an amino acid solution is disclosed for use with glucose, for administration especially to newborns, prematures and patients in the neonatal period, in which amino acids are present in proportion to the anabolic need of the body without heavily relying on the catabolic capability of the liver. On the basis that parenterally administered amino acids by-pass the liver in large part and thus avoid the major catabolic pathways of that organ, the amino acids composition is designed so that its administration does not change the pattern of the free amino acids of the peripheral blood.

Such prior approaches do not recognize or provide for the body's physiological response to trauma, sepsis or other injury. Failing to recognize the altered physiological state of a body suffering stress or injury, known amino acid solutions for intraveneous infusion have not presented the optimal configuration of amino acis to the patient. Consequently, they do not adequately or properly meet the nutritional requirements of a patient suffering stress or injury. Moreover, known methods of treatment and known amino acid solutions are not formulated or intended for use in connection with the nitrogen sparing, low or no carbohydrate, parenteral alimentation diet disclosed in U.S. Pat. No. 3,920,838. Especially where parenteral alimentation will be prolonged or where the stress or injury is severe, a nutritional therapy is needed, which is not only compatible with such low or no carbohydrate approach, but which also provides the optimal nutritonal regimen to promote patient recovery.

Accordingly, it is an object of the present invention to provide a pharmaceutical preparation comprising an amino acid composition for treatment of a patient obliged to receive nutritional requirements via parenteral or enteral administration, to optimize the nutritional regimen. In this regard, it is an object to provide an amino acid composition which is compatible for prolonged use in the nitrogen-sparing alimentation of a patient suffering stress or injury and which amino acid composition will promote wound healing, host defense, immune competence, non-sepsis and survival of the patient.

It is another object of the present invention to provide a pharmaceutical preparation comprising an amino acid solution suitable for use either alone or in conjunction with any nutritional therapy to promote wound healing, host defense, immune competence, non-sepsis and survival of a patient prevented from full and effective use of the gastro-intestinal tract and suffering stress or injury.

It is another object of the present invention to provide a pharmaceutical preparation comprising an amino acid composition in suitable hydrous concentrations for entral feeding.

It is a further object of the present invention to provide a method of treatment of a patient requiring entral or parenteral alimentation and suffering stress or injury.

It is a further object of the present invention to provide a method of treatment to promote wound healing, host defense, immune competence, non-sepsis and survival of a patient prevented from full and effective use of the gastro-intestinal tract and suffering stress or injury. In this regard, it is an object of the present invention to provide a unique, nitrogen-sparing nutritional therapy comprising administration of the novel pharmaceutical preparation of the invention via parenteral or enteral alimentation.

STATEMENT OF THE INVENTION

The invention described herein is a pharmaceutical preparation comprising a novel amino acid composition and a method of treatment employing it, for treatment of a patient suffering stress or injury, especially during periods of partial or total dysfunction or disuse of the gastrointestinal tract, to promote wound healing, host defense, immune competence, non-sepsis and survival. The pharmaceutical preparation of the invention comprises an amino acid composition in which at least about 70% and preferably as much as 100% of the amino acid content is the branched chain amino acids, leucine, isoleucine and valine, in the relative proportions of about a:b:c wherein a, b and c are each independent of the other and have a value of from 1 to 2. This novel branched chain amino acid composition can be entrally administered in any suitable hydrous concentrations. For parenteral administration it can comprise an infusion solution in which the total amino acid content is between about 2 and 6%, and preferably is 4% Most preferably, this novel amino acid solution is presented in modular form suitable for use either alone or together with other infusion solutions as one component of a nutritional regimen.

Another aspect of the present invention comprises a method of treatment for a patient suffering stress or injury, especially during periods of partial or total dysfunction or disuse of the gastrointestinal tract, to promote wound healing, host defense, immune competence, non-sepsis and survival. This novel method comprises the administration to the patient, via enteral or preferably, via parenteral infusion, of the novel amino acid composition of present invention. This method of treatment can comprise the entire nutritional therapy for the patient, or may comprise one part thereof.

In one preferred embodiment, the present invention comprises both administration of the novel amino acid composition and, simultaneously, the development and maintenance of a metabolic state simulating caloric starvation, by substantially withholding exogenous carbohydrates from the patient.

The present invention is characterized by improved wound healing, most defense immune competence, non-sepsis and/or survival by promoting protein synthesis in the patient. More specifically, both whole body protein, especially muscle and, most importantly, liver protein synthesis are promoted by the present invention. The invention is further characterized by reduction or near elimination of net nitrogen losses or even by net nitrogen gain, obtained most significantly by increased protein synthesis in both muscle and liver.

The invention described herein is based partly upon the recognition that the visceral tissues and secretory liver proteins, including albumin and transferrin, are critical to effective and successful patient wound healing, host defense, immune competence, non-sepsis and survival. Accordingly, increased liver protein synthesis will improve wound healing, etc. The invention is also based upon the discovery that the synthesis of whole body proteins, including liver proteins, during periods of stress or injury, is promoted and improved by the administration, either alone or in conjunction with other nutritional components, of the novel amino acid composition of the present invention consisting essentially of at least about 70% and preferably as much as 100% branched-chain amino acids (BCAA).

That such a nutritional regimen could increase the rate of liver protein synthesis, and in turn improve patient wound healing, etc., is not only surprising, but is also a radical departure from the art. That is, the newly discovered pharmacological effect of branched chain amino acid composition of the present invention, specifically, that such composition will improve visceral protein synthesis in the stressed body, is highly surprising since the primary site of metabolism of branched chain amino acids is well known to be in the muscle. Thus, previous investigations into branched chain amino acids have related to muscle metabolism and competition for neutral amino acid transport across the blood brain barrier and not to the effect of branched chain amino acid effect on protein synthesis in visceral tissue. This invention is based, in part, on newly discovered aspects of the body's response to stress or injury, involving the redistribution of body cell mass (protein and intracellular electrolytes) to sustain anabolic processes in most visceral organs, i.e. liver, bone marrow, kidney, gastrointestinal tract, lymph nodes, and other reticulo-endothelial system tissues. This redistribution of body cell mass has now surprisingly been discovered to be, in turn, dependent upon muscle energy metabolism and its interaction with oxidation of branched chain amino acids. The invention will be more fully understood from the detailed description and examples which follow.

Statistical analysis of data presented in the drawings was performed using analysis of variance (ANOVA), and least significant differences (LSD). Superscripts, a, b, and c designate differences at the 95% confidence level.

DETAILED DESCRIPTION OF THE INVENTION

In the description of this invention, the term "patient" is intended to mean any patient treated or treatable with or in accordance with the present invention. The reason for treatment by parenteral administration of amino acids is not critical, it being understood that such treatment is necessitated by the condition of the patient, whether it be due to trauma, sepsis, illness or other injury or stress.

The term "amino acid" as used herein is intended to means those amino acids used in patient therapy such as those L-amino acids, both essential and non-essential, conventionally infused into patients along with glucose. The term is intended to include α-keto analogs, di- or tripeptides.

The term "branched chain amino acid" and "BCAA" refer to the amino acids valine, leucine, and isoleucine, collectively.

The term "nitrogen balance" refers to the difference between intake and excretion of nitrogen. A negative nitrogen balance therefore refers to a loss situation where the excretion of nitrogen exceeds intake.

The term "starvation" means the condition known in the art to exist in a patent as a result of deprivation and lack of nourishment. As used in relation to patients treated in accordance with this invention, it is used in a slightly different sense as the patient will exhibit the energy metabolism of starvation, such as ketosis, due to hypocaloric feeding.

The term "parenteral administration" is used in its conventional sense to include intravenous infusion to peripheral veins as well as other methods known to the art.

The novel BCAA composition of the present invention, and its use, provide a significant advance over known infusion solutions and known nutritional therapies in promoting and even optimizing increased protein synthesis. Both whole body protein synthesis, especially muscle, and, most importantly, liver protein synthesis are increased more efficiently than with such known solutions and therapies. While it is known in the art that liver protein synthesis is of vital importance to effective wound healing, host defense, immune competence non-sepsis and survival, it is highly surprising and contrary to the teaching in the art that administration of BCAA could significantly and even most efficiently increase liver protein synthesis. In view of the known fact that BCAA are metablized virtually exclusively in muscle, and not at all in liver, it is highly surprising that pharmaceutical preparation comprising at least about 70% and preferably as much as 100% BCAA could promote liver protein synthesis in a stressed body, and thus promote and even optimize wound healing, host defense, immune competence, non-sepsis and survival.

Efficiency in this regard is of critical importance in view of the limited volume of infusion solution which can be accepted by the patient, and in view of the limited solubility of the nutrients in the infusion solution. Thus, an aqueous amino acid solution is limited to about 4% concentration at pH 6 and to about 6% at pH as low as 2 or as high as 9. Thus, the novel BCAA composition of the present invention can be presented in the form of an infusion solution at a concentration of from about 2% to 6% but preferably about 4% and is at about pH 6. The 6% solution, while within the scope of the invention, is less preferred in view of the necessity of pre-infusion pH-adjustment. For convenience, reference herein will be to the 4% solution with the understanding that solutions of from 2 to 6% are intended to be included therein.

In view of these limitations on the amount of nutritional support which can be provided to a patient, it is typically impossible to replace all of the normal nutritional intake of a patient suffering partial or total dysfunction or disuse of the gastrointestinal tract. In that situation, if the patient is also suffering stress or injury it becomes of vital importance to administer a nutritional therapy which most efficiently promotes wound healing, host defense, immune competence, non-sepsis and survival. The novel BCAA composition of the present invention provides such a nutritional therapy. It has now been discovered that this novel composition, whether used alone or together with other nutrients, provides, on a weight-for-weight basis, the greatest increase in liver protein synthesis and, consequently, the most efficient support for patient wound healing, most defense, immune competence, non-sepsis and survival.

Figure 1:
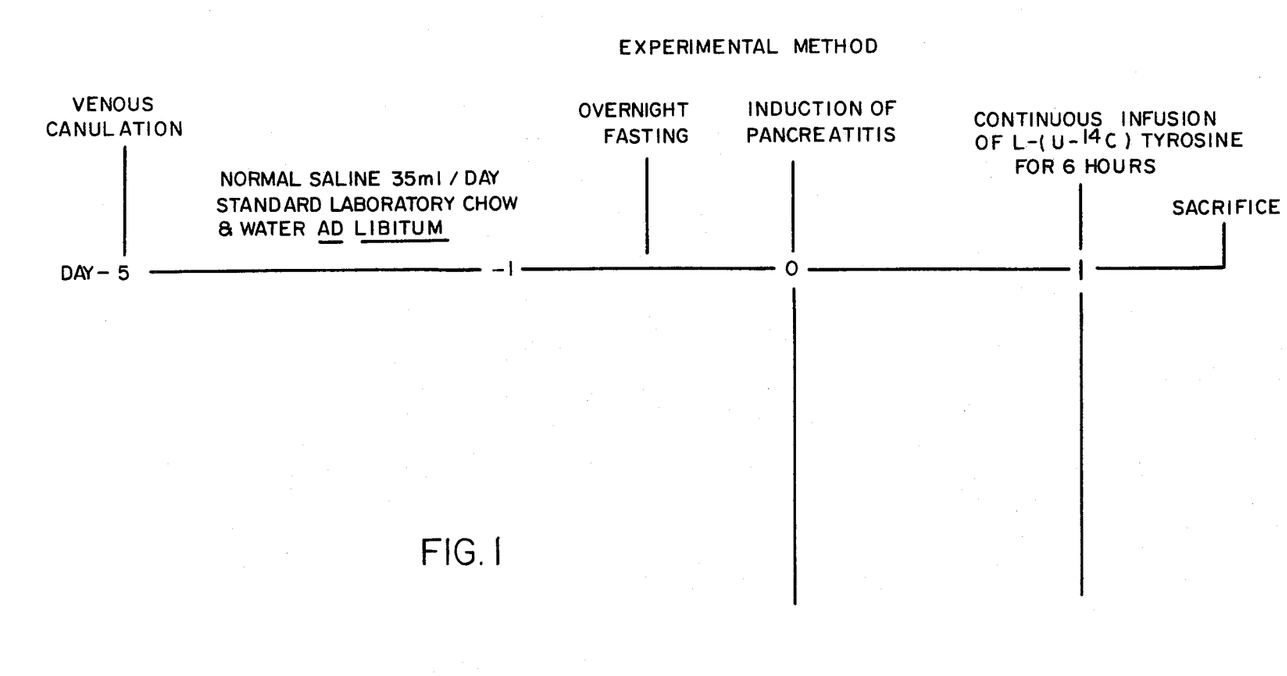
FIG. 1 is a diagrammatic illustration of the experimental method used to establish a stress model.

While not intending to be bound by theory, an explanation of the now discovered function of the novel BCAA composition in facilitating the body's physiological response to stress or injury, as presently understood, is useful to an understanding of the invention. For this purpose, FIGS. 1 to 4 show a "stress model," that is, a profile of the body's physiological response to stress or injury. Specifically, a comparison of healthy versus traumatized rats is presented for its applicability of mammals generally, and to humans particularly. FIG. 1 graphically illustrates the experimental method employed to establish the stress model. The following example further describes the method.

EXAMPLE 1

Sprague-Dawley CD rats (200–250 gm) underwent venous canulation and were returned to metabolic units where they received normal saline, 35 ml/day, and were allowed to consume standard laboratory chow and water ad libitum for four days. The rats were then fasted overnight, following which pancreatitis was induced in all but a control group. For the next 30 hours both control rats and pancreatitis rats were fasted. During the final 6 hours of feeding, all rats received continuous infusion of L-(U-$^{14}$C)tyrosine to determine whole body amino acid oxidation and fractional synthesis of whole body protein. The rats were then sacrificed.

Figure 2:
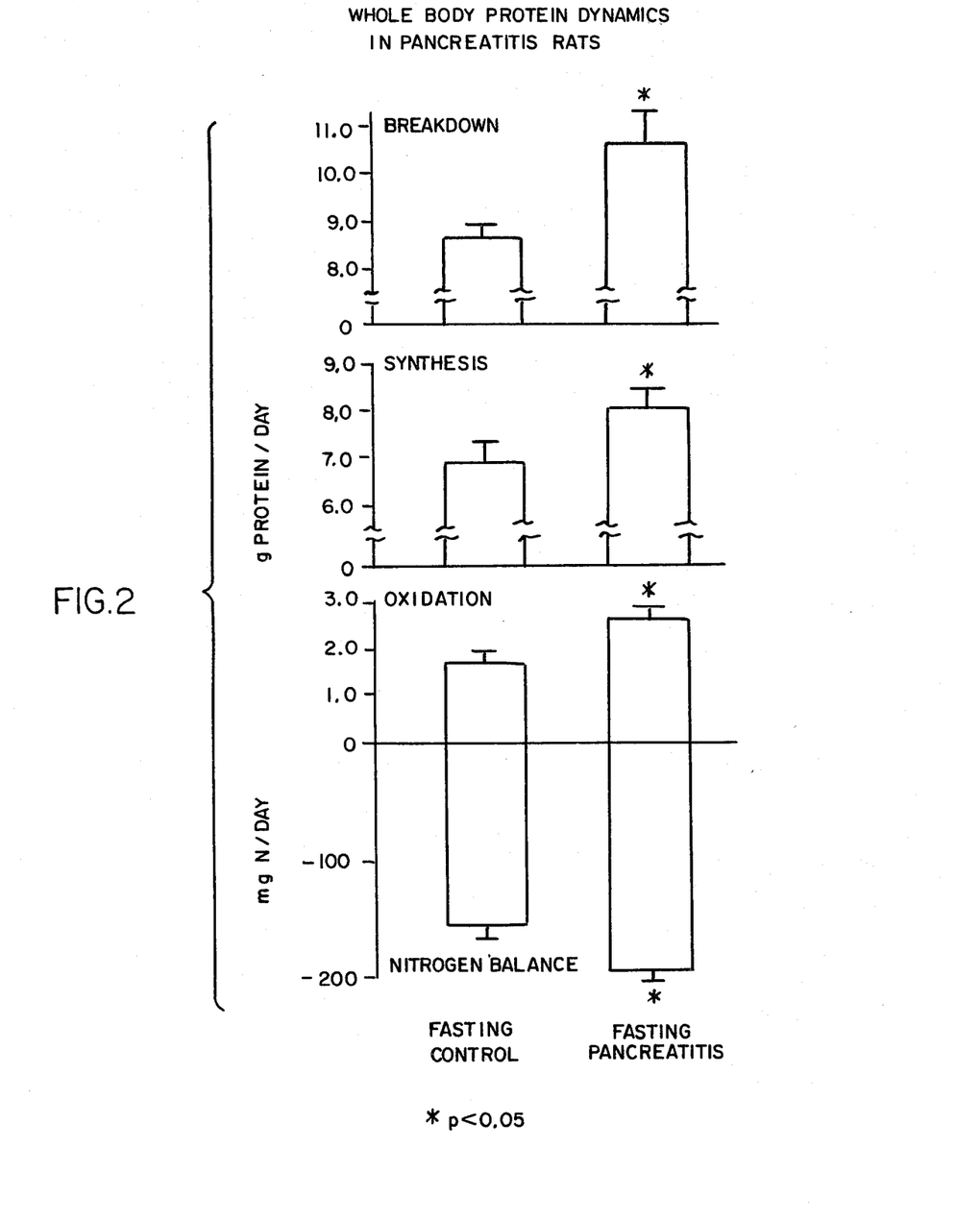
FIG. 2 is a graphical illustration of whole body protein dynamics in the stressed and unstressed body.
Figure 3:
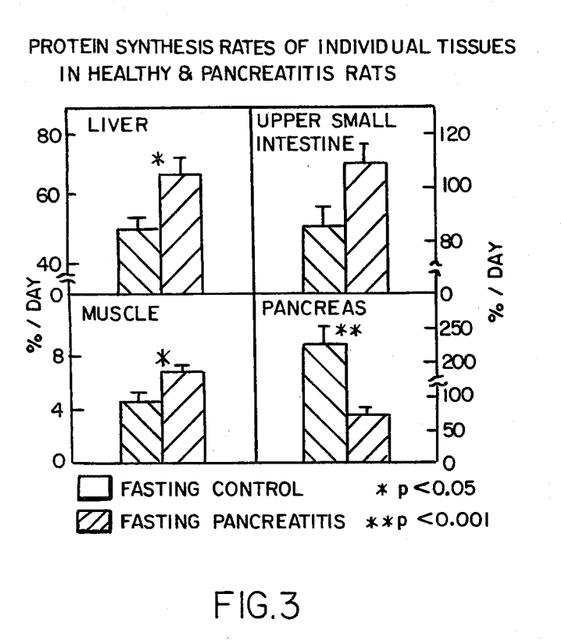
FIG. 3 is a graphical illustration of protein synthesis rates of individual tissues in the stressed and unstressed body.
Figure 4:
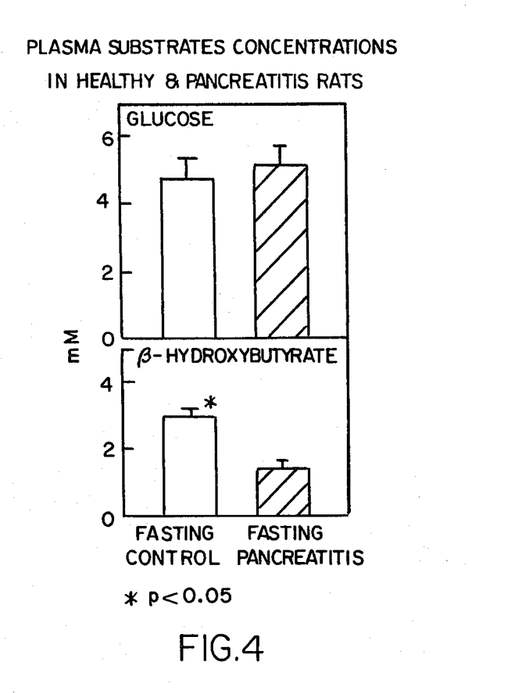
FIG. 4 is a graphical illustration of plasma substrate concentrations in the stressed and unstressed body.

Results: FIG. 2 graphically illustrates and compares the whole body protein dynamics in the traumatized and non-traumatized fasting rats. Protein breakdown, synthesis and oxidation were increased in the traumatized rats. Net nitrogen loss was also increased over the fasting control. FIG. 3. illustrates and compares the percent per day protein synthesis rates of individual tissues. The body's response to stress is shown to include increased synthesis of muscle, upper small intestine and especially liver protein. As would be expected, pancreas protein synthesis is lowered in the pancreatitis rats. A significant aspect of the stress model is illustrated in FIG. 4, showing the plasma concentration levels of glucose and of -hydroxybutyrate, a ketone body produced by the liver. Stress is shown to have resulted in significant changes in the blood concentrations of energy fuel substrates. The glucose level is higher in the stress model, while the level of ketone bodies is decreased.

It is well known that an important function of dietary protein is to furnish the substrate required for tissue and organ protein synthesis. However, as illustrated by the stress model of Example 1, during stress or trauma, infection, or other injury, significant alternations in protein metabolism occur as part of the body's natural response thereto. In particular, protein metabolism is altered such that there is a net breakdown of muscle protein to amino acid to provide substrate to sustain whole-body protein synthesis. Reutilization of these amino acids for visceral protein synthesis, particularly acute phase proteins, liver secretory proteins, and leukocyctic activity is a major component of the metabolic response to injury.

However, excessive loss of lean body mass through protein breakdown is ultimately harmful to patient recovery and survival. The present invention now provides a nutritional composition and nutritional therapy for a stressed body which supports and increases the functional synthesis of whole body protein, especially muscle and, more importantly, mixed liver proteins, more effectively than known nutritional solutions and therapies. Moreover, the present invention reduces net nitrogen loss more efficiently than other previously known therapies.

That the present invention provides a pharmacological effect not due merely to the ingestion of α-amino nitrogen, is apparent from the fact that the same results are not obtained even with isonitrogenous diets consisting of L-alanine, (which amino acid might have been expected to produce optimum results since it is metabolized in both liver and muscle and thus supports protein sparing mechanisms in both.) Moreoever, since BCAA are not metabolized in the liver, the effectiveness of the present invention to promote liver protein synthesis is highly surprising.

That this pharmacological effect is not reproduceable by any other amino acid configurations in similar amounts is believed due to the unique ketogenic nature of the BCAA. The BCAA are ketogenic precursors which allow the stressed body to utilize ketone bodies which are being depleted by the injury or stress. FIG. 4 shows the depletion of the ketone body -hydroxybutyrate in the stress model of Example 1. In the stressed body there is decreased oxidation of non-protein energy substrates, including glucose, as shown by the increased plasma concentration of glucose in the stressed body (FIG. 4). Hyperinsulinemia results and fosters reesterification of free fatty acids within the adipocyte, thereby decreasing net free fatty acid release and thus its oxidation rate. Deficiencies in these competing endogenous energy fuels in the stressed body create an energy deficit met by increased branched chain amino acid oxidation. While the regulatory mechanism remains hypothetical, it is presently best understood as competition by carbodydrate, fat, and protein metabolites of Co-A-SH. This complex physiological response to injury can be counter-productive when nutritional intake is limited by the need to rely on parenteral alimentation. In that circumstance, if the essential amino acids necessary to support wound healing and homeostasis, are not otherwise available, the body will sacrifice lean body mass. Thus, in the stressed body, the availability of BCAA is believed to be the major determinant of gluconeogenesis, ketogenesis and of the rate of protein catabolism. More specifically, the novel BCAA composition of this invention provides for keto-adaptation and provides for protein synthesis of hepatic export proteins such as albumin, transferrin, immunoglobulins, and C-3 complement all of which are important for host defense and recovery from injury, sepsis, infection and other actute illness. Thus, oxidation of branched chain amino acids during periods of post injury and starvation may be a rate limiting step in the mobilization and redistribution of body amino acids for synthesis of visceral and acute phase proteins.

The foregoing explanation of the pharmacological function of the BCAA composition of the invention is a stressed body having a limited source of alternate ketogenic precursers, is intended to facilitate an understanding of the invention. It is, however, theoretical in part, and might ultimately prove incomplete and/or otherwise inaccurate. In any event there is no intent to be bound by such theroretical explanation.

While the novel BCAA composition of the present invention preferably consists essentially only of branched chain amino acids, alternately it can comprise some amount of other essential or non-essential amino acids or other components such as other nutritional components, for example glucose. Thus, the novel BCAA solution can comprise as much as 20 or even 30% of amino acids other than the branched chain amino acids. It should be recognized however, that a corresponding decrease in the efficiency of the infusion solution to promote wound healing etc., would be expected with reduction in the total amount of BCAA intake.

The ratio of the branched chain amino acids in the novel composition of the invention, i.e. A:B:C wherein A, B and C each independently of the other has a value of from 1 to 2, provides the maximum efficacy and efficiency in promoting wound healing, non-sepsis, immune competence and survival, while the compositions outside that ratio range would be efficacious, but less efficient. The ratio A:B:C, as defined, is necessitated, for optimal efficiency, by the integration of the individual metabolism of each BCAA, and by the amino acid pool size and turnover rate.

According to the nutritional therapy aspect of the present invention, such other nutritional components may be presented via the same solution with the BCAA or via separate solutions administered simultaneously or alternately with the novel BCAA composition. The novel BCAA composition is preferably administered as a BCAA solution by parenteral infusion, such as by I.V. While peripheral vein infusion is preferred as the more routine method, administration can alternately be via central vein or the portal vein system. Alternate to, or in addition to the parenteral administration of the novel BCAA solution, the method of treatment of this invention can comprise the enteral alimentation of the BCAA composition in various hydrous concentrations, administered, for example, using an artificial gut system typically used for such enteral feeding. In this use, the BCAA need not be fully dissolved into solution, and thus concentrations considerably higher than 2 to 6% can be used and such higher concentration solutions are within the scope of the invention.

Regarding dosage, the novel BCAA solution of the present invention will be most useful when the patient must rely on nutritional intake via parenteral administration. In that case, especially during the initial stage of treatment, the BCAA composition of the invention can be presented as a BCAA solution as described above. The solution is preferably infused in the maximum amount tolerable by the patient. Typically no more than 500 to 1000 ml per day of the novel BCAA solution would be administered, but even 1500 and/or more can be administered. If other infusion solutions are also administered, there would be a corresponding decrease in the amount of the BCAA solution. Using the preferred 4% BCAA solution, the rate of infusion is preferably adjusted so that from about 20 to 40 grams of BCAA are delivered per day, or approximately 0.3 to 0.7 gm of BCAA per kg body weight per day.

When the BCAA composition of the present invention is presented as a BCAA solution, it is most preferably in the form of a modular unit adapted for direct connection to I.V. tubing for parenteral infusion. The modular unit can conveniently contain, for example, 500 ml of the novel BCAA solution. In an alternative embodiment, the BCAA composition can be in anhydrous form suitable for mixing with water and, if desired, other nutrients. In a further alternative embodiment, a modular unit can contain a pre-measured amount of the BCAA composition in anhydrous form, and be adapted to receive that volume of water (sterile water if for parenteral infusion) suitable to compose a unit dose of the novel BCAA composition as a solution or other hydrous concentration.

It should be noted that these branched chain amino acids can be α-keto analogs, di- or tripeptides and can be combined in aqueous solution with other amino acids, suitable electrolytes, fats, carbohydrates, alcohols, pH adjusters and the like, typically used in parenteral administration, without departing from the scope of the invention.

While the BCAA composition of the present invention will be effective and useful in any nutritional therapy to promote wound healing, etc. in a stressed body, one most preferred aspect of the present invention is a method of treatment comprising administration of the BCAA composition and simultaneously developing and maintaining the natural metabolic state of injury, illness, etc., wherey endogenous fat is readily mobilized, as previously described. In this nutritional therapy, the novel BCAA composition is administered while substantially limiting or totally withholding exogenous high calorie nutrients such as carbohydrates from the patient to limit the counter regulatory effects of such exogenous calories. Use of the BCAA composition of the present invention in such therapy has now been discovered to promote or even to optimize patient wound healing, host defense, immune competence, nonsepsis and survival in a patient suffering partial or total dysfunction or disuse of the gastrointestinal tract, by (as presently understood,) most efficently increasing whole body protein synthesis, including muscle and especially liver protein synthesis, while minimizing net nitrogen loss or even producing a net nitrogen gain.

EXAMPLE 2

Sprague-Dawley CD rats were prepared to the point of trauma as described in Example 1. Following the induction of pancreatitis in all but a control group, the pancreatitis rats were each given one of 5 diets for a 30 hour period: (1) fasting; (2) BCAA (200 mg N); (3) L-alanine (200 mg N) (4) glucose (7.2 cal); and (5) fat (7.2 cal). The control group was fasted. During the final six hours of feeding, all rats received continuous infusion of a tracer quantity of L-(U-$^{14}$C)tyrosine to determine whole body endogenous amino acid oxidation and fractional synthesis of protein according to the method of James W P T, Garlick P J, Sender P M, et al., *Studies of Amino Acid And Protein Metabolism In Normal Man With L-(U-$^{14}$C)-tyrosine*, Clin. Sci. Mol. Med. 50–525 (1976); and Blackburn G L, Moldawer L L, Usui S, et al., *Branched Chain Amino Acid Administration And Metabolism During Starvation, Injury And Infection*, Surgery, Vol. 87 (1979), both of which are incorporated herein by reference.

Figure 5:
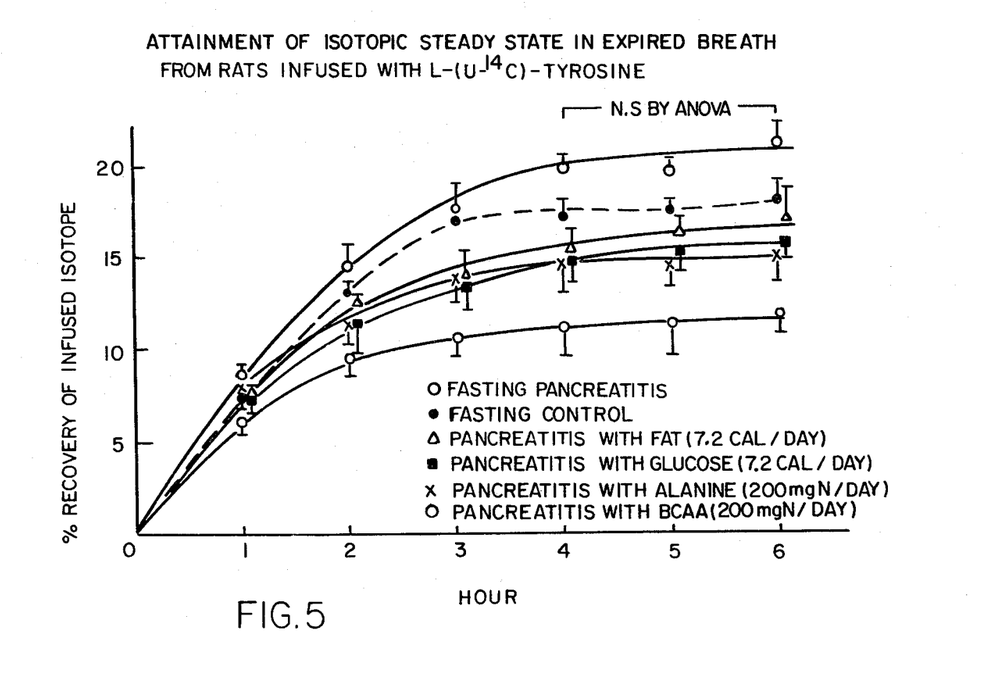
FIG. 5 is a graphical illustration of the attainment, over time, of an isotopic steady state in the percent recovery of infused isotope in expired breath from the unstressed body and from the stressed body receiving one of various diets.

Results: FIG. 5 shows the steady state attained in the percentage recovery of the infused isotope in the expired breath of the rats. The BCAA diet produced the greatest reduction of endogenous tyrosine oxidation, to a degree not obtained by the isonitrogenous L-alanine diet. Taking the kinetics of tyrosine metabolism as representative of amino acid in general, the BCAA diet most improved the reutilization of amino acids released by protein breakdown, and, correspondingly, most reduced the oxidation of endogenous amino acids.

Figure 6:
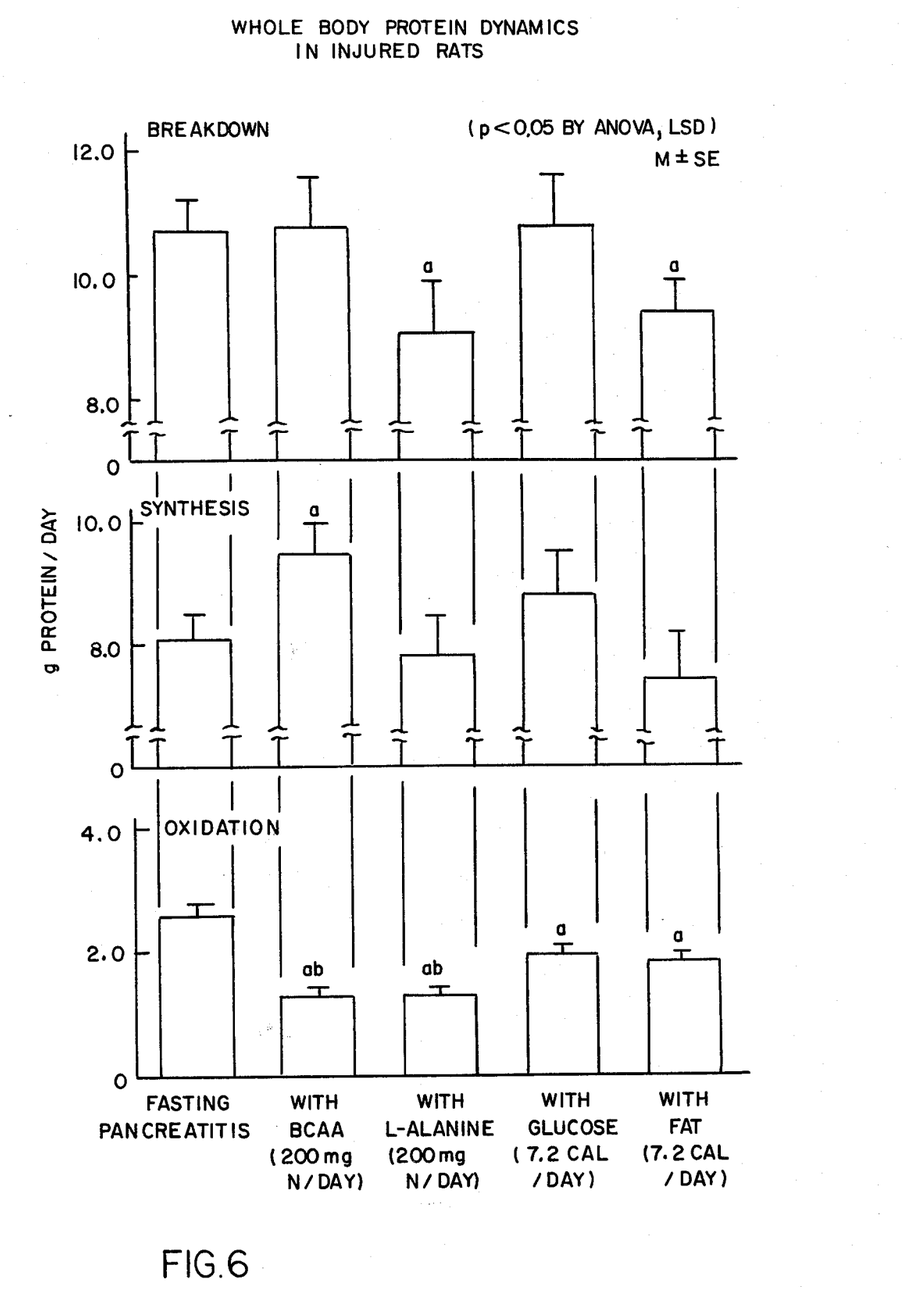
FIG. 6 is a graphical illustration of whole body protein dynamics in the stressed body receiving one of various diets.
Figure 7:
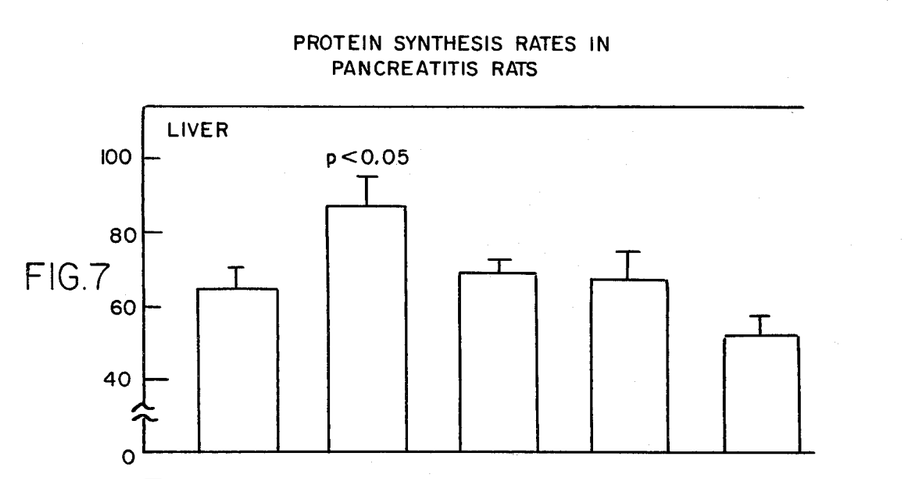
FIG. 7 is a graphical illustration of liver protein synthesis rates in the stressed body receiving one of various diets.
Figure 8:
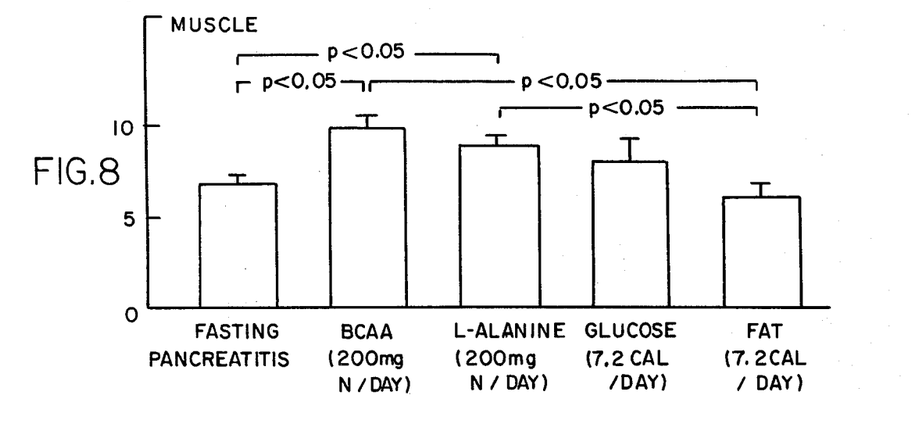
FIG. 8 is a graphical illustration of muscle protein synthesis rates in the stressed body receiving one of various diets.
Figure 9:
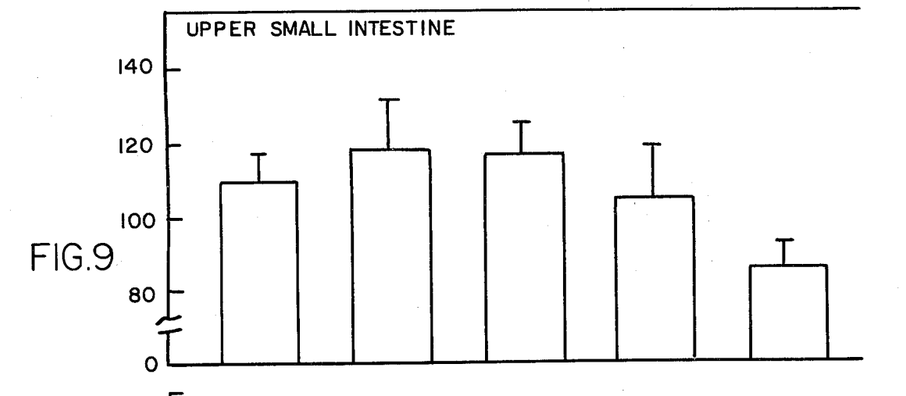
FIG. 9 is a graphical illustration of upper small intestine protein synthesis rates in the stressed body receiving one of various diets.
Figure 10:
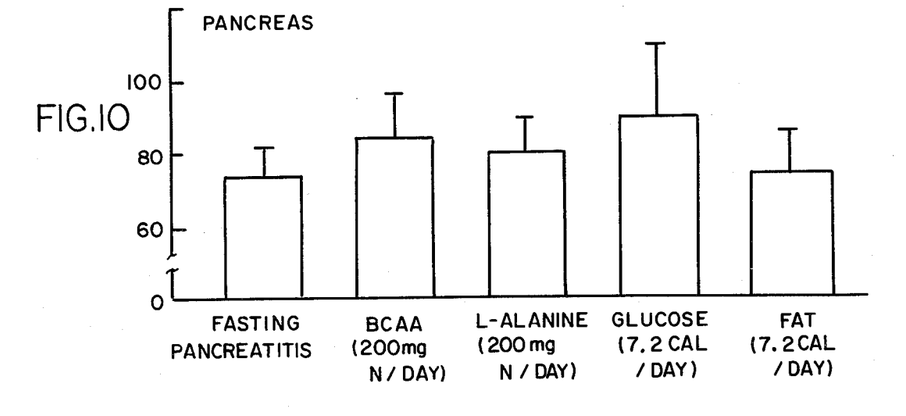
FIG. 10 is a graphical illustration of pancreas protein synthesis rates in the stressed body receiving one of various diets.

FIG. 6 graphically illustrates and compares whole body protein dynamics in the stressed and unstressed rats. It can be seen that oxidation of whole body protein is lowest and roughly equivalent for the two isonitrogenous diets, that is, the BCAA and the L-alanine diets. Of critical significance however, is the increased whole body protein synthesis produced only by the BCAA diet. More specifically, FIGS. 7–10 graphically illustrated and compare the protein synthesis rates in the stressed rats receiving the various diets. The hypocaloric, 100% BCAA infusion solution shows the most effective promotion of protein synthesis in pancreas (except for the glucose diet), upper small intestine, muscle and most importantly, liver.

Figure 11:
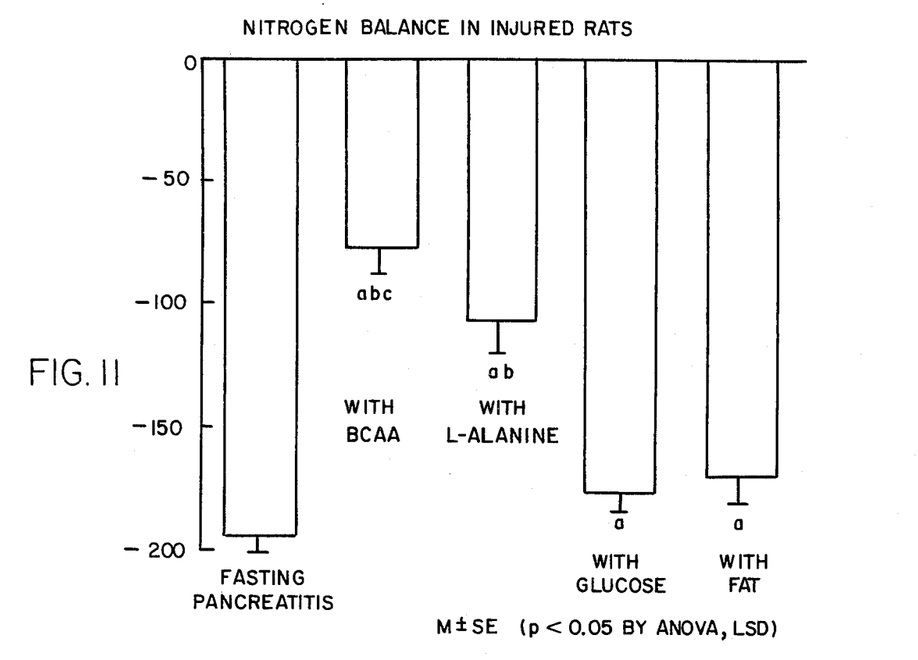
FIG. 11 is a graphical illustration of the net nitrogen balance in the stressed body receiving one of various diets.

FIG. 11 graphically illustrates and compares the nitrogen balance achieved with the various diets. The hypocaloric 100% BCAA diet results in the most favorable nitrogen balance.

Figure 12:
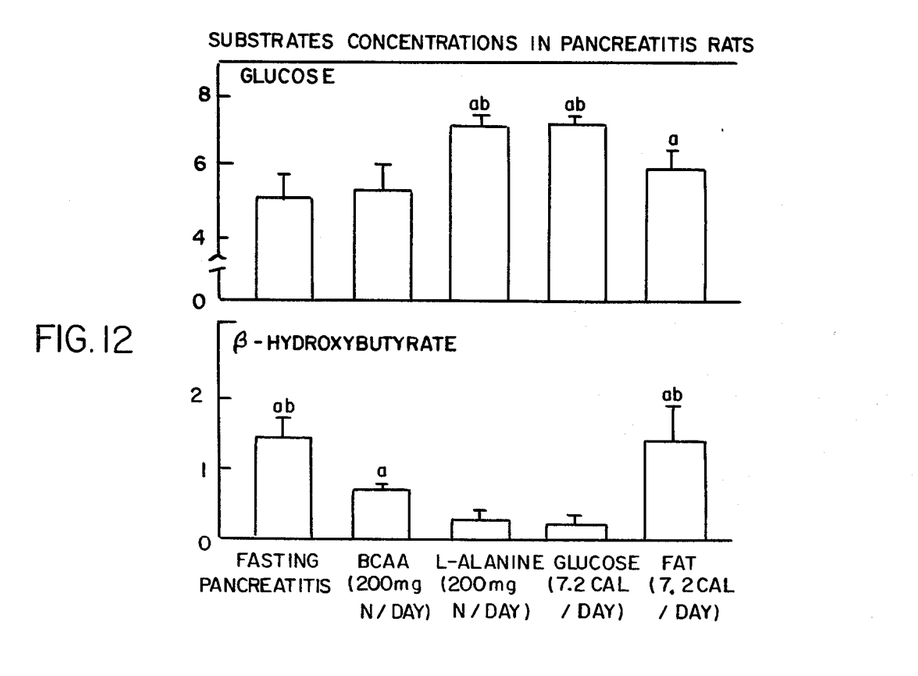
FIG. 12 is a graphical illustration of plasma substrate concentrations in the stressed body receiving one of various diets.

FIG. 12 graphically illustrates and compares the effect of the various diets on plasma glucose and ketone body concentrations in the stressed body. The hypocaloric, 100% BCAA diet is shown to promote a ketogenic state, rather than a glucogenic state.

The results of Example 2 demonstrate a pharmacological effect not explained solely by the nitrogen content of the novel BCAA infusion solution of the invention, in view of the poorer nitrogen balance achieved with the isonitrogenrac L-Alanine diet. While each diet improved nitrogen balance over fasting in the stressed body, the nitrogen sparing mechanisms are shown to be different. Table I outlines this phenomena.

TABLE I

| | WHOLE BODY PROTEIN DYNAMICS | | |
|---|---|---|---|
| | BREAKDOWN | SYNTHESIS | OXIDATION |
| BCAA | — | ↑↑↑ | ↓↓ |
| L-ALANINE | ↓↓ | — | ↓↓ |
| FAT | ↓↓ | — | ↓ |
| GLUCOSE | — | — | ↓ |

Moreover, only the novel BCAA composition effectively stimulated liver protein synthesis. While muscle protein synthesis was significantly increased with both BCAA and L-Alanine adminstration, and no significant change in protein synthesis was observed in either upper small intestine or pancreas with any nutrient therapy, these are far less important to patient wound healing, etc. than the liver proteins. Accordingly, the novel BCAA composition and method of treatment of the present invention are unique in the ability to reduce net nitrogen loss by a nitrogen sparing mechanism which promotes patient recovery and survival more efficiently than can be achieved with any other known isonitrogenous, isocaloric nutritional therapy. There is also better phagocytic activity and a decrease in loss of all amino acids in the urine, supporting the importance of the branched chain amino acid composition to enhance visceral tissue function (i.e. liver, bone marrow, and kidney).

EXAMPLE 3

Fasted-septic rats were infused with isovolemic diets containing: (1) BCAA (210 mg Nitrogen/day); (2) L-Alanine (210 mg Nitrogen/day); or (3) were fasted.

Figure 13:
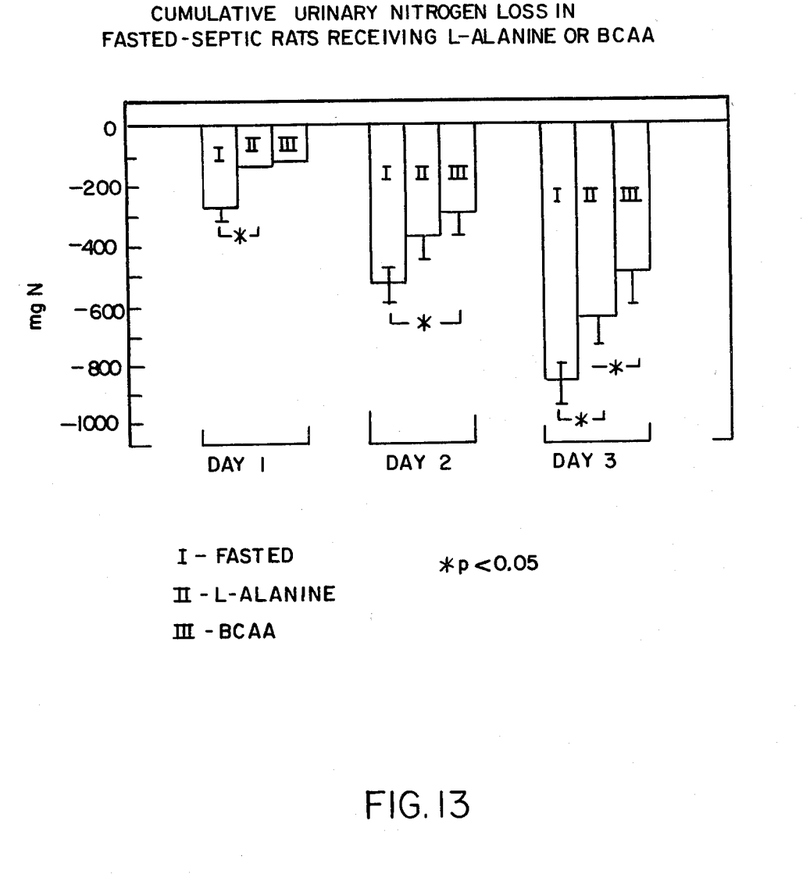
FIG. 13 graphically illustrates urinary nitrogen loss in septic rats receiving one of various diets.

Results: As shown in FIG. 13, the BCAA diet reduced nitrogen loss by 30% as compared to fasting the isonitrogenous L-Alanine diet did not produce comparable results. Thus, the nitrogen sparing mechanism can not be explained as merely the result of providing α-amino acid nitrogen and/or amino acid calories.

EXAMPLE 4

Ten middle aged patients with acute hepacellular failure encephapathy asociated with an eventual admission mortality of 60% were studied. Baseline blood samples were taken before commencing them on a study period of 6 days during which they received intravenous nutrition supplying 1500–2000K cal per day as glucose and intralipid, salt poor albumin where indicated and a supplement of 40 g of leucine, isoleucine and valine in a 1:1:1 ratio, for 3 days followed by 40 g of a standard complete amino acid mixture for the remaining period. The nitrogen balace was estimated throughout the test period and blood samples were taken on day 3 and 6.

Results: Mean values for the 10 patients are shown in Table II:

TABLE II

| (# P < 0.05 by ANOVA) | | | | |
|---|---|---|---|---|
| | Valine | Iso-leucine mM/ml | Leucine | $N_{bal}$ gn/d |
| BASELINE | .13 | .01 | .05 | — |
| SD | ±.05 | ±.01 | ±.04 | — |
| BCCA | .321 # | .107 # | .133 # | +1.75 |
| SD | ±.119 | ±.04 | ±.07 | ±4.47 |
| A.A. | .13 | .03 | .06 | # −1.37 |
| SD | ±.08 | ±.03 | ±.05 | ±4.78 |

The increased levels of the BCAA are accompanied by a markedly improved nitrogen balance a net nitrogen gain, whereas the complete amino acid mixture resulted in a net nitrogen loss.

I claim:

1. A method of nutritional therapy for a patient suffering from physical injury or metabolic stress, said patient having a normalized urinary nitrogen excretion of at least about 15 gr/dayand having at the same time at least a partial dysfunction of the gastrointestinal tract in order to at least partially sustain protein synthesis in said patient comprising parenterally administering to said patient an effective nutritional therapy amount of an amino acid parenteral composition in which 70 to 100% of the amino acid content consists of the branched chain amino acids, leucine, isoleucine and valine in relative proportions a:b:c wherein a, b and c are independent of each other and have a value from 1 to 2 to provide effective nutritional therapy for said patient.

2. The method of claim 1 in which the parenteral composition is a solution containing a concentration of 2 to 6% total amino acids.

3. The method of claim 1 in which the injury is trauma.

4. A method of nutritional therapy for a patient said patient having a normalized urinary nitrogen excretion of about 15 gr/day and having at least a partial dysfunction of the gastrointestinal tract in association with sepsis in order to at least partially sustain protein syntheses in said patient comprising parenterally administering to said patient an effective nutritional therapy amount of an amino acid parenteral composition in which 70 to 100% of the amino acid content consists of the branched chain amino acids consisting of leucine, isoleucine and valine in relative proportions a:b:c: wherein a, b, c are independent of each other and have a value from 1 to 2 to provide effective nutritional therapy for said patient.

5. The method of claim 4 in which the enteral composition is a solution containing a concentration of 2 to 6% total amino acids.

* * * * *